(12) United States Patent
Hobson et al.

(10) Patent No.: US 7,875,588 B2
(45) Date of Patent: Jan. 25, 2011

(54) METHODS OF THERAPY USING PHARMACEUTICAL COMPOSITION FOR THROMBIN PEPTIDE DERIVATIVES

(75) Inventors: David W. Hobson, Boerne, TX (US); Roger S. Crowther, League City, TX (US); Darrell H. Carney, Dickinson, TX (US); Andrew Po Kwan Tang, Webster, TX (US)

(73) Assignee: Orthologic Corp., Tempe, AZ (US)

( * ) Notice: Subject to any disclaimer, the term of this patent is extended or adjusted under 35 U.S.C. 154(b) by 646 days.

(21) Appl. No.: 11/903,877

(22) Filed: Sep. 25, 2007

(65) Prior Publication Data

US 2009/0054343 A1 Feb. 26, 2009

Related U.S. Application Data

(62) Division of application No. 11/027,923, filed on Dec. 30, 2004, now Pat. No. 7,291,596.

(60) Provisional application No. 60/533,730, filed on Dec. 31, 2003.

(51) Int. Cl.
*A61K 38/00* (2006.01)
*A61K 38/36* (2006.01)

(52) U.S. Cl. ............................ 514/12; 514/2; 514/298; 514/357; 514/566; 424/9.1

(58) Field of Classification Search .................. 514/12, 514/2, 298, 357, 566; 424/9.1
See application file for complete search history.

(56) References Cited

U.S. PATENT DOCUMENTS

| 4,409,334 | A | 10/1983 | Lill et al. |
| 5,352,664 | A | 10/1994 | Carney et al. |
| 5,500,412 | A | 3/1996 | Carney et al. |
| 2002/0128202 | A1 | 9/2002 | Carney et al. |

*Primary Examiner*—Chih-Min Kam
(74) *Attorney, Agent, or Firm*—Foley & Lardner, LLP.; Steven G. Davis (57) ABSTRACT

Disclosed are pharmaceutical compositions comprising a thrombin peptide derivatives and a chelating agent and/or a pharmaceutically acceptable thiol-containing compound. The pharmaceutical compositions optionally further comprise an antioxidant. Also, disclosed are methods for activating the non-proteolytically activated thrombin receptor in a subject in need of such treatment. The methods comprise the step of administering an effective amount of a thrombin peptide derivative in the pharmaceutical composition described above.

23 Claims, 3 Drawing Sheets

FIG. 3

METHODS OF THERAPY USING PHARMACEUTICAL COMPOSITION FOR THROMBIN PEPTIDE DERIVATIVES

RELATED APPLICATIONS

This application is a divisional of U.S. application Ser. No. 11/027,923, filed Dec. 30, 2004, now U.S. Pat. No. 7,291,596, which claims the benefit of U.S. Provisional Application No. 60/533,730, filed on Dec. 31, 2003. The entire teachings of the above applications are incorporated herein by reference.

BACKGROUND OF THE INVENTION

Thrombin is a serine protease present in blood plasma in the form of a precursor, pro-thrombin. Thrombin has been known for growth-promoting activity for a wide variety of cells from various tissues by activation of a specific cell surface receptor known as the non-proteolytically activated thrombin receptor. For example, thrombin has been shown to promote angiogenesis, the development of new blood vessels, and to stimulate endothelial cell proliferation (see, e.g., U.S. Pat. Nos. 5,352,664, 5,500,412, the contents of which are incorporated herein by reference in its entirety).

Thrombin peptide derivatives are synthetic analogs of thrombin which have an amino acid sequence derived at least in part from that of thrombin and are active at the non-proteolytically activated thrombin receptor. For example, thrombin peptide derivatives from amino acids 508-530 of human pro-thrombin have been described by the present inventors for promoting thrombin receptor mediated cell stimulation and for their use in the treatment of wounds, stimulating bone growth and cartilage growth or repair, and promoting cardiac tissue repair (see, e.g., U.S. Pat. Nos. 5,352,664, 5,500,412, WO 02/07748, WO 02/005836, WO 02/004008 and WO 03/013569, the contents of which are incorporated herein by reference in their entirety).

Thrombin peptide derivatives show great potential as pharmaceuticals because of their therapeutic activity for the treatment of wounds, stimulating bone growth and cartilage growth and promoting cardiac repair. Unfortunately, however, thrombin peptide derivatives are highly susceptible to dimerization. For example, TP508, an example of a thrombin peptide derivative having the amino acid sequence H-Ala-Gly-Tyr-Lys-Pro-Asp-Glu-Gly-Lys-Arg-Gly-Asp-Ala-Cys-Glu-Gly-Asp-Ser-Gly-Gly-Pro-Phe-Val-NH$_2$ (SEQ ID NO: 4), dimerizes over time, and has a half-life of about 2 to about 4 hours in certain buffered solutions at neutral pH and a half-life of about 7 days at high peptide concentrations in sterile saline (See Example 1).

It therefore is necessary to develop methods to maintain the purity of thrombin peptide derivatives over extended time periods and prevent or reduce dimerization, so that thrombin peptide derivatives have a long storage life and it is possible to deliver precise and reproducible dosages, even after storage for prolonged periods of time.

SUMMARY OF THE INVENTION

It has now been found that a pharmaceutical composition that includes a thrombin peptide derivative and a dimerization inhibitor retains the monomeric form of the thrombin peptide derivative essentially free of dimers. A dimerization inhibitor is a compound which inhibits or reduces dimerization of a thrombin peptide derivative. Dimerization inhibitors include chelating agents and/or thiol-containing compounds. In one example, TP508 in the presence of a chelating agent, ethylenediaminetetraacetic acid (EDTA), retained its monomeric form greater than 90% by weight over 2 weeks at 4° C. (see Example 3). An antioxidant can also be used in combination with the chelating agent and/or the thiol-containing compound. Based on this discovery, the invention provides a novel pharmaceutical composition comprising the thrombin peptide derivative and the dimerization inhibitor, and a method for activating the non-proteolytically activated thrombin receptor in a subject in need of such treatment.

One embodiment of the present invention is a pharmaceutical composition comprising a thrombin peptide derivative and a chelating agent and/or a pharmaceutically acceptable thiol-containing compound. The pharmaceutical composition further optionally comprises an antioxidant.

Another embodiment of the invention is a method for activating the non-proteolytically activated thrombin receptor in a subject in need of such treatment. The methods comprise the step of administering an effective amount of a pharmaceutical composition described herein.

Advantages of the pharmaceutical composition of the present invention include a longer storage life for thrombin peptide derivatives than was previously possible. Therefore, it is possible to deliver precise and reproducible dosages with thrombin peptide derivatives, even after storage for prolonged periods of time. The pharmaceutical composition can be used in the treatment and/or prevention of diseases and/or conditions in which angiogenesis and cell proliferation would be beneficial. The pharmaceutical composition can be used to accelerate, for example, bone growth, cartilage growth or repair, and the healing of wounds such as diabetic ulcers and to stimulate bone growth at sites where bone growth would not occur in the absence of treatment (e.g., non-union fracture, voids or gaps in bones or bone grafts). The pharmaceutical composition of the present invention can also be used to prevent restenosis in patients after angioplasty and regenerate blood vessels in cardiac tissue.

DETAILED DESCRIPTION OF THE INVENTION

Applicants have found that thrombin peptide derivatives retain their monomeric form essentially free of dimers in the presence of a dimerization inhibitor such as a chelating agent or a thiol-containing compound, e.g., greater than 90% free by weight over 2-month time period and preferably greater than 95% free by weight over 2-month time period (Example 3). The chelating agent and the thiol-containing compound can be used together or separately to prevent or reduce dimerization of thrombin peptide derivatives. An antioxidant optionally can be used in combination with the chelating agent and/or the thiol-containing compound.

A "chelating agent," as used herein, is a compound having multiple sites (two, three, four or more) which can simultaneously bind to a metal ion or metal ions such as, for example, lead, cobalt, iron or copper ions. The binding sites typically comprise oxygen, nitrogen, sulfur or phosphorus. For example, salts of EDTA (ethylenediaminetetraacetic acid) can form at least four to six bonds with a metal ion or metal ions via the oxygen atoms of four acetic acid moieties (—CH$_2$C(O)O$^-$) and the nitrogen atoms of ethylenediamine moieties (>N—CH$_2$—CH$_2$—N<) of EDTA. It is understood that a chelating agent also includes a polymer which has multiple binding sites to a metal or metal ions. Preferably, a chelating agent of the invention is non-toxic and does not cause unacceptable side effects at the dosages being administered. As a chelating agent of the invention, a copper-chelating agent is preferable. A "copper-chelating agent" refers to a chelating agent which can bind to a copper ion or copper ions. Examples of the copper-chelating agent include ethylenediaminetetraacetic acid (EDTA), penicillamine, trientine, N,N-diethyldithiocarbamate (DDC), 2,3,2'-tetraamine (2,3,2'-tet), neocuproine, N,N,N',N'-tetrakis(2-pyridylmethyl)ethylenediamine (TPEN), 1,10-phenanthroline (PHE), tetraethylenepentamine (TEPA), triethylenetetraamine and tris(2-carboxyethyl)phosphine (TCEP). Additional chelating agents are diethylenetriaminepentacetic acid (DTPA) and bathophenanthroline disulfonic acid (BPADA). EDTA is a preferred chelating agent. Typical amounts of a chelating agent present in the pharmaceutical compositions of the instant invention is in a range of between about 0.00001% and about 0.1% by weight, preferably between about 0.0001% and about 0.05% by weight.

A "pharmaceutically acceptable thiol-containing compound", as used herein, is a compound which comprises at least one thiol (—SH) group and which does not cause unacceptable side effects at the dosages which are being administered. Examples of the pharmaceutically acceptable thiol-containing compound include thioglycerol, mercaptoethanol, thioglycol, thiodiglycol, cysteine, thioglucose, dithiothreitol (DTT) and dithio-bis-maleimidoethane (DTME). Typically, between about 0.001% and about 5% by weight, preferably between about 0.05% and about 1.0% by weight of a pharmaceutically acceptable thiol-containing compound is present in the pharmaceutical compositions of the invention.

An "antioxidant," as used herein, is a compound which is used to prevent or reduce an oxidation reaction caused by an oxidizing agent such as oxygen. Examples of the antioxidant include tocopherol, cystine, methionine, glutathione, tocotrienol, dimethyl glycine, betaine, butylated hydroxyanisole, butylated hydroxytoluene, vitamin E, ascorbic acid, ascorbyl palmitate, thioglycolic acid and antioxidant peptides such as, for example, turmerin. Typically, between about 0.001% and about 10% by weight, preferably between about 0.01% and about 5%, more preferably between about 0.05% and about 2.0% by weight of an antioxidant is present in the pharmaceutical compositions of the invention.

It is understood that certain chelating agents or thiol-containing compounds may also function as an antioxidant, for example, tris(2-carboxyethyl)phosphine, cysteine or dithiothreitol. Other types of commonly used antioxidants, however, do not contain a thiol group. It is also understood that certain thiol-containing compounds may also function as a chelating agent, for example, dithiothreitol. Other types of commonly used chelating agents, however, do not contain a thiol group. It is also understood that the pharmaceutical compositions of the instant invention can comprise more than one chelating agent, thiol-containing compound or antioxidant. That is, for example, a chelating agent can be used either alone or in combination with one or more other suitable chelating agents.

A "thrombin receptor agonist" refers to a compound which stimulates or activates the non-proteolytically activated thrombin receptor (NPAR) (R. Horvat, et. al., *J. Cell Sci.* 108, 1155-1164, 1995). Compounds which stimulate NPAR are said to be NPAR agonists. NPAR is a high-affinity thrombin receptor present on the surface of most cells. This NPAR component is largely responsible for high-affinity binding of thrombin, proteolytically inactivated thrombin, and thrombin derived peptides to cells. NPAR appears to mediate a number of cellular signals that are initiated by thrombin independent of its proteolytic activity. An example of one such signal is the upregulation of annexin V and other molecules identified by subtractive hybridization (see Sower, et. al., *Experimental Cell Research* 247:422 (1999)). NPAR is therefore characterized by its high affinity interaction with thrombin at cell surfaces and its activation by proteolytically inactive derivatives of thrombin and thrombin derived peptide agonists as described below. NPAR activation can be assayed based on the ability of molecules to stimulate cell proliferation when added to fibroblasts in the presence of submitogenic concentrations of thrombin or molecules that activate protein kinase C as disclosed in U.S. Pat. Nos. 5,352,664 and 5,500,412. The entire teachings of these patents are incorporated herein by reference. NPAR agonists can be identified by this activation or by their ability to compete with $^{125}$I-thrombin binding to cells. Thrombin peptide derivatives are examples of the thrombin receptor agonist. A thrombin peptide derivative is a polypeptide with less than about fifty amino acids, preferably less than about thirty-three amino acids and have sufficient homology to the fragment of human thrombin corresponding to pro-thrombin amino acids 508-530 (Ala-Gly-Tyr-Lys-Pro-Asp-Glu-Gly-Lys-Arg-Gly-Asp-Ala-Cys-Glu-Gly-Asp-Ser-Gly-Gly-Pro-Phe-Val: SEQ ID NO: 3), so that the thrombin peptide derivative has at least 25% of the activity of TP508 at NPAR, preferably by at least 50%. Thrombin peptide derivatives described herein preferably have between about 14 and 23 amino acids, more preferably between about 19 and 23 amino acids. Optionally, the thrombin peptide derivatives described herein can have C-terminal amides and/or an acylated N-terminus.

An "acylated N-terminus" is an N-terminus in which the nitrogen of the N-terminal amino acid residue is acylated. For example, acylated N-terminal amino acid residues have the formula: R3C(O)—NH—CHR$_a$C(O)—. R$_a$ is an amino acid side chain, and R3 is hydrogen (—H) or a C$_1$-C$_6$ alkyl group, preferably methyl (—CH$_3$) group. A preferred acyl group is an acetyl group. An "—H" at the N-terminus indicates that the N-terminus is unsubstituted; and no designation at the N-terminus indicates that the terminus is acylated or unsubstituted.

A "C-terminal amide" is an amide at the C-terminal amino acid residue in which the alpha carboxylic acid is replaced with an amide. For example, amidated C-terminal amino acid residues have the formula: —NH—CH(R$_a$)C(O)—NR4R5. R$_a$ is an amino acid side chain, and R4 and R5 are independently —H, a C$_1$-C$_6$ alkyl group or, taken together with the nitrogen atom to which they are bonded, a heterocyclic group such as a piperidinyl, morpholinyl, thiomorphinyl or pyrollidinyl. Preferably, the C-terminal amide is a carboxamide (—C(O)NH$_2$). As used herein, "—NH$_2$" at the C-terminus indicates a C-terminus carboxamide; "—OH" at the C-terminus indicates that the peptide has a free C-terminus; and no designation at the C-terminus indicates that the peptide is amidated at the C-terminus or has a free C-terminus.

Preferably, the N-terminus of a thrombin peptide derivative is free (i.e., unsubstituted) and the C-terminus is free (i.e., unsubstituted) or amidated, preferably a carboxamide (i.e., —C(O)NH$_2$).

A preferred thrombin peptide derivative for use in the disclosed composition consists of the following amino acid sequence: R1-Ala-Gly-Tyr-Lys-Pro-Asp-Glu-Gly-Lys-Arg- Gly-Asp-Ala-Cys-Glu-Gly-Asp-Ser-Gly-Gly-Pro-Phe-Val-R2: SEQ ID NO: 1. R1 is —H or R3-C(O)—; R2 is —OH or —NR4R5; R3 is —H or $C_1$-$C_6$ alkyl group (preferably —$CH_3$); and R4 and R5 are independently —H, a $C_1$-$C_6$ alkyl group or, taken together with the nitrogen atom to which they are bonded, a non-aromatic heterocyclic group such a piperidinyl, morpholinyl, thiomorphinyl or pyrollidinyl (preferably R4 and R5 are both —H). Preferably R1 is —H and R2 is —$NH_2$; or R1 is —H and R2 is —OH. Alternatively, a thrombin peptide derivative which can be used in the disclosed formulation has the amino acid sequence of SEQ ID NO: 5: R1-Asp-Asn-Met-Phe-Cys-Ala-Gly-Tyr-Lys-Pro-Asp-Glu-Gly-Lys-Arg-Gly-Asp-Ala-Cys-Glu-Gly-Asp-Ser-Gly-Gly-Pro-Phe-Val-Met-Lys-Ser-Pro-Phe-R2. R1 and R2 are as described above. It is understood, however, that zero, one, two or three amino acids at positions 1-9 and 15-23 in the thrombin peptide derivative can differ from the corresponding amino acid in SEQ ID NO: 1. It is also understood that zero, one, two or three amino acids at positions 1-14 and 20-33 in the thrombin peptide derivative can differ from the corresponding amino acid in SEQ ID NO: 5. Preferably, the amino acids in the thrombin peptide derivative which differ from the corresponding amino acid in SEQ ID NO: 1 or SEQ ID NO: 5 are conservative substitutions, and are more preferably highly conservative substitutions. Alternatively, an N-terminal truncated fragment of the thrombin peptide derivative of SEQ ID NO: 1 having at least fourteen amino acids or a C-terminal truncated fragment of the thrombin peptide derivative of SEQ ID NO: 1 having at least eighteen amino acids can be used in the formulation. Another alternative is an N-terminal truncated fragment of the thrombin peptide derivative of SEQ ID NO: 5 having at least nineteen amino acids or a C-terminal truncated fragment of the thrombin peptide derivative of SEQ ID NO: 5 having at least twenty-three amino acids can be used in the formulation.

A "C-terminal truncated fragment" refers to a fragment remaining after removing an amino acid or block of amino acids from the C-terminus. An "N-terminal truncated fragment" refers to a fragment remaining after removing an amino acid or block of amino acids from the N-terminus. It is to be understood that the terms "C-terminal truncated fragment" and "N-terminal truncated fragment" encompass acylation at the N-terminus and/or amidation at the C-terminus, as described above. It is also understood that the invention includes C-terminal truncated fragments and N-terminal truncated fragments with the modifications of amino acid residues made in the original thrombin peptide derivatives before the truncation, as described above.

Another preferred thrombin peptide derivative for use in the disclosed composition consists of the amino acid sequence of SEQ ID NO: 2: R1-Ala-Gly-Tyr-Lys-Pro-Asp-Glu-Gly-Lys-Arg-Gly-Asp-Ala-Cys-$X_1$-Gly-Asp-Ser-Gly-Gly-Pro-$X_2$-Val-R2. $X_1$ is Glu or Gln; $X_2$ is Phe, Met, Leu, His or Val; and R1 and R2 are as described above. Another preferred thrombin peptide derivative for use in the disclosed composition consists of the amino acid sequence of SEQ ID NO: 6: R1-Asp-Asn-Met-Phe-Cys-Ala-Gly-Tyr-Lys-Pro-Asp-Glu-Gly-Lys-Arg-Gly-Asp-Ala-Cys-$X_1$-Gly-Asp-Ser-Gly-Gly-Pro-$X_2$-Val-Met-Lys-Ser-Pro-Phe-R2. $X_1$ is Glu or Gln; $X_2$ is Phe, Met, Leu, His or Val; and R1 and R2 are as described above. Alternatively, an N-terminal truncated fragment of the thrombin peptide derivative of SEQ ID NO: 2 having at least fourteen amino acids or a C-terminal truncated fragment of the thrombin peptide derivative of SEQ ID NO: 2 having at least eighteen amino acids can be used in the formulation. Another alternative is an N-terminal truncated fragment of the thrombin peptide derivative of SEQ ID NO: 6 having at least nineteen amino acids or a C-terminal truncated fragment of the thrombin peptide derivative of SEQ ID NO: 6 having at least twenty-three amino acids can be used in the formulation.

Another preferred thrombin peptide derivative for use in the disclosed composition comprises the amino acid sequence of SEQ ID NO: 3: Ala-Gly-Tyr-Lys-Pro-Asp-Glu-Gly-Lys-Arg-Gly-Asp-Ala-Cys-Glu-Gly-Asp-Ser-Gly-Gly-Pro-Phe-Val. This peptide is preferably 23 amino acids in length.

Another preferred thrombin peptide derivative for use in the disclosed composition is TP508. TP508 is an example of a thrombin peptide derivative with the amino acid sequence of SEQ ID NO: 4: H-Ala-Gly-Tyr-Lys-Pro-Asp-Glu-Gly-Lys-Arg-Gly-Asp-Ala-Cys-Glu-Gly-Asp-Ser-Gly-Gly-Pro-Phe-Val-$NH_2$. Another example of a thrombin peptide derivative has the amino acid sequence of SEQ ID NO: 7: H-Ala-Gly-Tyr-Lys-Pro-Asp-Glu-Gly-Lys-Arg-Gly-Asp-Ala-Cys-Glu-Gly-Asp-Ser-Gly-Gly-Pro-Phe-Val-OH ("deamide TP508").

A thrombin peptide derivative represented by Structural Formula (I), preferably between 14 and 23 amino acids in length, can also be used in the disclosed formulation:

$$\text{Asp-Ala-R} \tag{I}$$

where R is a serine esterase conserved domain. Serine esterases, e.g., trypsin, thrombin chymotrypsin and the like, have a region that is highly conserved. "Serine esterase conserved domain" refers to a polypeptide having the amino acid sequence of one of these conserved regions or is sufficiently homologous to one of these conserved regions such that the thrombin peptide derivative retains NPAR activating ability. In one embodiment, the serine esterase conserved sequence has the amino acid sequence of SEQ ID NO. 8 (Cys-Glu-Gly-Asp-Ser-Gly-Gly-Pro-Phe-Val) or a C-terminal truncated fragment of a polypeptide having the amino acid sequence of SEQ ID NO. 8.

Other examples of thrombin peptide derivatives which can be used in the disclosed formulation include N-terminal truncated fragments of TP508 (or deamide TP508), the N-terminal truncated fragments having at least fourteen amino acids or C-terminal truncated fragments of TP508 (or deamide TP508), the C-terminal truncated fragments having at least eighteen amino acids. Optionally, these peptides are amidated at the C-terminus and unsubstituted at the N-terminus. In another alternative, optionally, these peptides are amidated at C-terminus as —C(O)—$NH_2$ and unsubstituted at N-terminus.

A "conservative substitution" is the replacement of an amino acid with another amino acid that has the same net electronic charge and approximately the same size and shape. Amino acids with aliphatic or substituted aliphatic amino acid side chains have approximately the same size when the total number carbon and heteroatoms in their side chains differs by no more than about four. They have approximately the same shape when the number of branches in the their side chains differs by no more than one. Amino acids with phenyl or substituted phenyl groups in their side chains are considered to have about the same size and shape. Listed below are five groups of amino acids. Replacing an amino acid in a polypeptide with another amino acid from the same group results in a conservative substitution:

Group I: glycine, alanine, valine, leucine, isoleucine, serine, threonine, cysteine, and non-naturally occurring amino acids with $C_1$-$C_4$ aliphatic or $C_1$-$C_4$ hydroxyl substituted aliphatic side chains (straight chained or monobranched).

Group II: glutamic acid, aspartic acid and non-naturally occurring amino acids with carboxylic acid substituted $C_1$-$C_4$ aliphatic side chains (unbranched or one branch point).

Group III: lysine, ornithine, arginine and non-naturally occurring amino acids with amine or guanidino substituted $C_1$-$C_4$ aliphatic side chains (unbranched or one branch point).

Group IV: glutamine, asparagine and non-naturally occurring amino acids with amide substituted $C_1$-$C_4$ aliphatic side chains (unbranched or one branch point).

Group V: phenylalanine, phenylglycine, tyrosine and tryptophan.

A "highly conservative substitution" is the replacement of an amino acid with another amino acid that has the same functional group in the side chain and nearly the same size and shape. Amino acids with aliphatic or substituted aliphatic amino acid side chains have nearly the same size when the total number carbon and heteroatoms in their side chains differs by no more than two. They have nearly the same shape when they have the same number of branches in their side chains. Examples of highly conservative substitutions include valine for leucine, threonine for serine, aspartic acid for glutamic acid and phenylglycine for phenylalanine. Examples of substitutions which are not highly conservative include alanine for valine, alanine for serine and aspartic acid for serine.

In one embodiment, the disclosed pharmaceutical composition comprises a thrombin peptide derivative and either a chelating agent or a pharmaceutically acceptable thiol-containing compound. Preferably, the disclosed pharmaceutical composition comprises a thrombin peptide derivative; the chelating agent; and the pharmaceutically acceptable thiol-containing compound. As a chelating agent of the invention, a copper-chelating agent such as described previously is preferable.

Alternatively, the disclosed pharmaceutical composition comprises a thrombin peptide derivative and a chelating agent, preferably a copper-chelating agent and/or a pharmaceutically acceptable thiol-containing compound, and further comprises an antioxidant.

In a preferred embodiment, the disclosed pharmaceutical composition comprises a thrombin peptide derivative and a chelating agent, preferably a copper-chelating agent, and an antioxidant. In a more preferred embodiment, the disclosed pharmaceutical composition comprises a thrombin peptide derivative and a chelating agent, preferably a copper-chelating agent, and methionine. Preferably, the chelating agent is EDTA.

Preferably, the disclosed pharmaceutical composition is in a pH range of between about 5 and about 6, more preferably, between about 5.5 and about 6. In one example, the pharmaceutical composition, which comprises a thrombin peptide derivative and a chelating agent, preferably a copper-chelating agent, and an antioxidant, is in a pH range of between about 5 and about 6, more preferably, between about 5.5 and about 6. In this composition, preferably, the antioxidant is methionine.

Another embodiment of the invention is a method for activating the non-proteolytically activated thrombin receptor in a subject in need of such treatment. The method comprises the step of administering an effective amount of a pharmaceutical composition described herein.

A "subject" is preferably a human, but can also be an animal in need of treatment with a thrombin receptor agonist, e.g., companion animals (e.g., dogs, cats, and the like), farm animals (e.g., cows, pigs, horses and the like) and laboratory animals (e.g., rats, mice, guinea pigs and the like).

Subjects "in need of treatment" with a thrombin receptor agonist, are subjects with diseases and/or conditions that can be treated with thrombin receptor agonists and thrombin peptide derivatives to achieve a beneficial therapeutic and/or prophylactic result. A beneficial outcome includes a decrease in the severity of symptoms or delay in the onset of symptoms, increased longevity and/or more rapid or more complete resolution of the disease or condition. For example, a subject in need of treatment requires cell proliferation involving chondrocytes, angiogenesis, bone growth, cardiac repair, wound healing, cartilage growth or repair, or inhibition of restenosis.

Thrombin peptide derivatives have been shown to stimulate proliferation of endothelial cells, fibroblasts, and keratinocytes (see, e.g., U.S. Pat. Nos. 5,500,412 and 5,352,664, the contents of which are incorporated herein by reference in their entirety). Thrombin peptide derivatives can therefore be used to promote healing in acute wounds such as, for example, burns, dermal wounds, surgical wounds and bone fractures. In addition, thrombin peptide derivatives have recently been shown to be particularly effective in promoting the healing of chronic wounds such as, diabetic ulcers, venous ulcers, and pressure sores (see, e.g., WO 03/013569, the contents of which are incorporated herein by reference in their entirety). Thrombin peptide derivatives have also been shown to stimulate cartilage growth or repair and the growth of chondrocytes (see, e.g., WO 02/07748, the contents of which are incorporated herein by reference in their entirety). Thus, thrombin peptide derivatives can be used to stimulate cartilage growth or repair or chondrocyte growth and repair in, for example patients with osteoarthritis or joint injuries. Other uses for thrombin peptide derivatives include stimulating bone growth to promote healing of simple fractures, non-union fractures, voids and gaps in bone and bone grafts, preventing restenosis in patients after angioplasty and promoting the regeneration of blood vessels in cardiac tissue (see, e.g., WO 02/005836, WO 02/004008, and US Patent Application Publication No. 2002/0128202, the contents of which are incorporated herein by reference in their entirety).

Induced bone growth can also be therapeutically beneficial at certain sites within a subject (referred to as "ectopic" sites) where bone tissue would not normally be found, such as a site in need of a bone graft or bone fusion. Fusions are commonly used to treat lower back pain by physically coupling one or more vertebrae to its neighbor. The bone created by such a fusion is located at a site not normally occupied by bone tissue. Induced bone growth at these ectopic sites can act as a "graft substitute" whereby induced bone growth between the vertebrae takes the place of a graft and obviates the need for a second operation to harvest bone for the grafting procedure. Induction of bone growth is also needed for treating acquired and congenital craniofacial and other skeletal or dental anomalies (see e.g., Glowacki et al., *Lancet* 1: 959 (1981)); performing dental and periodontal reconstructions where lost bone replacement or bone augmentation is required such as in a jaw bone; and supplementing alveolar bone loss resulting from periodontal disease to delay or prevent tooth loss (see e.g., Sigurdsson et al., *J. Periodontol.*, 66: 511 (1995)).

The pharmaceutical composition of the instant invention comprising a thrombin peptide derivative can therefore be used in such treatments as described above.

An "effective amount" is the quantity of a thrombin peptide derivative in the pharmaceutical composition of the present invention that results in an improved clinical outcome of the condition being treated with the thrombin peptide derivative compared with the absence of treatment. The amount of thrombin peptide derivatives administered will depend on the degree, severity, and type of the disease or condition, the amount of therapy desired, and the release characteristics of the pharmaceutical formulation. It will also depend on the subject's health, size, weight, age, sex and tolerance to drugs. Typically, the thrombin peptide derivative is administered for a sufficient period of time to achieve the desired therapeutic effect. For the indication of cardiac repair, typically between about 0.1 µM to 10 µM or more typically between about 50 to 250 µg per a single injection of the thrombin peptide derivative is administered to a damaged tissue for a satisfactory increase in the rate of repair. For the indication of cartilage growth or repair, typically between about 0.1 :g per a single application and about 1 mg per a single application of the thrombin peptide derivative, preferably between about 25 :g and about 100 :g per 20 cubic mm, is administered. For the treatment of chronic dermal ulcer, typically between about 0.1 :g and about 1 mg per a single application, preferably between about 1 :g and about 100 :g per a single application, of the thrombin peptide derivative is administered. Particularly, one to seven applications per week of the thrombin peptide derivative is administered for the treatment of chronic dermal ulcer. For the indication of bone growth, typically between about 1 :g and about 1 mg per day, preferably between about 5 :g and about 100 :g per day, of the thrombin peptide derivative is administered.

In another embodiment, the disclosed pharmaceutical composition further comprises a pharmaceutically acceptable carrier as part of the pharmaceutical composition. Suitable pharmaceutical carriers may contain inert ingredients which do not inhibit the biological activity of a thrombin peptide derivative and the function of a chelating agent, a thiol-containing compound and an antioxidant. The carriers should be biocompatible, i.e., non-toxic, non-inflammatory, non-immunogenic and devoid of other undesired reactions at the administration site. Pharmaceutically acceptable carriers vary according to the route of administration selected and the indication being treated. Examples of pharmaceutically acceptable carriers include, for example, saline, aerosols, commercially available inert gels, or liquids supplemented with albumin, methylcellulose or a collagen matrix. Standard pharmaceutical formulation techniques can be employed, such as those described in Remington's Pharmaceutical Sciences, Mack Publishing Company, Easton, Pa.

The compositions of the present invention can be solutions, suspensions, emulsions, syrups, gels, ointments, lotions, creams, pastes, putty, extrusions, microparticles, capsules, tablets or the like.

A gel formulation is commonly used when the thrombin peptide derivative is being used to promote cardiac repair and wound healing. Gels are comprised of a base selected from an oleaginous base, water, or an emulsion-suspension base. The oleaginous base contains fixed oils or hydrocarbons, such as white petrolatum or mineral oil, or an absorbent base, e.g., consisting of an absorbent anhydrous substance or substances, for example, anhydrous lanolin. The emulsion-suspension base comprises an oil phase (internal phase) containing typically fixed oils, hydrocarbons, and the like, such as waxes, petrolatum, mineral oil, and the like, and an aqueous phase (continuous phase) comprising water and any water-soluble substances such as added salts. The two phases are stabilized by use of an emulsifying agent, for example, a surface active agent such as sodium lauryl sulfate, hydrophilic colloids such as acacia colloidal clays, beegum, and the like. To the base is added a gelling agent which forms a matrix in the base, increasing its viscosity to a semisolid consistency. Examples of suitable gelling agents include hydroxypropyl cellulose, acrylic acid polymers, polymers of poly(ethylene oxide) or copolymers of ethylene and propylene oxide (see Cao et al., *J. Biomater. Sci* 9:475 (1998) and Sims et al., *Plast Reconstr. Surg.* 98.843 (1996), the entire teachings of which are incorporated herein by reference). Pluronic gels are non-toxic block copolymers of ethylene oxide and propylene oxide. They exhibit thermosetting properties that allow them to exist as viscous liquids at room temperature, but as gels at body temperatures. The active ingredients are added to the formulation at the desired concentration at a point preceding addition of the gelling agent or can be mixed after the gelation process. Gels for the treatment of promoting wound healing may be administered in a local topical administration. The preparation of gels is described in Example 7.

Formulations for a local topical administration other than gels include ointments and creams. Ointments are typically prepared using the oleaginous base described previously. Creams generally comprise the emulsion-suspension base described previously. Following the formation of the base, the active ingredients are added in the desired concentration.

In another preferred embodiment, the disclosed pharmaceutical compositions are lyophilized pellets which can be reconstituted prior to use. The lyophilized pellets commonly used for indications such as bone growth and cardiac repair. The lyophilized compositions optionally comprise a bulking agent in addition to the other active ingredients described previously. Suitable bulking agents include mannitol, lactose, cellulose, sorbitol, dextrose, dextran, polydextrose, maltitol, xylitol, isomalt, erythritol, glycerol and the like. The lyophilized compositions can be reconstituted to form solutions, and may contain auxiliary substances such as wetting or emulsifying agents, pH buffering agents, viscosity enhancing additives, preservatives and the like, depending upon the route of administration and the preparation desired.

The pharmaceutical compositions of the present invention are typically sustained release formulations for indications such as bone growth, cartilage growth or repair and cardiac repair. The sustained release formulations can provide for continuous release of medication over a period of hours. Polymers are often used to form the sustained release formulations. Examples of the polymers include poly ∀-hydroxy esters such as polylactic acid/polyglycolic acid (PLGA) homopolymers and copolymers, polyphosphazenes (PPHOS), polyanhydrides and poly(propylene fumarates) (PPF).

Polylactic acid/polyglycolic acid (PLGA) homo and copolymers are well known in the art as sustained release vehicles. The rate of release can be adjusted by the skilled artisan by variation of polylactic acid to polyglycolic acid ratio and the molecular weight of the polymer (see Anderson, et al., *Adv. Drug Deliv. Rev.* 28:5 (1997), the entire teachings of which are incorporated herein by reference). The incorporation of poly(ethylene glycol) into the polymer as a blend to form microparticle carriers allows further alteration of the release profile of the active ingredient (see Cleek et al., *J. Control Release* 48:259 (1997), the entire teachings of which are incorporated herein by reference). Ceramics such as calcium phosphate and hydroxyapatite can also be incorporated into the formulation to improve mechanical qualities. PLGA microparticles can also be mixed with pluronic gels or collagen to prevent aggregation and to make the microparticles suitable for direct injection. Preparation of PLGA microspheres of TP508 is described in detail in WO 03/061690, the contents of which are incorporated herein by reference in their entirety.

PPHOS polymers contain alternating nitrogen and phosphorous with no carbon in the polymer backbone, as shown below in Structural Formula (I):

(I)

The properties of the polymer can be adjusted by suitable variation of side groups R and R' that are bonded to the polymer backbone. For example, the degradation of and drug release by PPHOS can be controlled by varying the amount of hydrolytically unstable side groups. With greater incorporation of either imidazolyl or ethylglycol substituted PPHOS, for example, an increase in degradation rate is observed (see Laurencin et al., *J Biomed Mater. Res.* 27.963 (1993), the entire teachings of which are incorporated herein by reference), thereby increasing the rate of drug release.

Polyanhydrides, shown in Structural Formula (II), have well defined degradation and release characteristics that can be controlled by including varying amounts of hydrophobic or hydrophilic monomers such as sebacic acid and 1,3-bis(p-carboxyphenoxy)propane (see Leong et al., *J. Biomed. Mater. Res.* 19:941 (1985), the entire teachings of which are incorporated herein by reference). To improve mechanical strength, anhydrides are often copolymerized with imides to form polyanhydride-co-imides. Examples of polyanhydride-co-imides that are suitable for orthopaedic applications are poly(trimellitylimido-glycine-co-1,6-bis(carboxyphenoxy) hexane and pyromellityimidoalanine:1,6-bis(p-carboxyphenoxy)hexane copolymers.

(II)

The pharmaceutical compositions of the instant invention can be administered by any suitable route, locally or systemically. Typically, the route of administration depends on the type of formulation being used and the indication treated. Topical administration is commonly used for treating wounds. For the topical administration, the pharmaceutical compositions are typically creams, gels, ointments or aerosols, as described previously in detail. For certain indications such as stimulating bone growth, cartilage repair or growth and cardiac repair, it is advantageous to inject or implant the pharmaceutical composition of the instant invention directly to the treatment site.

For the indications in need of cardiac repair, cartilage growth or repair and bone growth, the pharmaceutical compositions of the invention are typically injectable forms. For example, the disclosed injectable compositions can be injected directly to the site in need of bone growth and can conveniently be used to fill voids and fuse bones without the need for invasive surgery. "Injectable" means that the material can be injected by syringe through a standard needle used for injecting solutions, pastes or gels. The injectable compositions may be administered intravenously or directly at the site in need of treatment. The injectable compositions may further include physiological saline, bacteriostatic saline (saline containing about 0.9% mg/mL benzyl alcohol), phosphate-buffered saline, Hank's solution, Ringer's-lactate, or liquids supplemented with albumin, methyl cellulose, or hyaluronic acid. The injectable compositions may also include polymers of poly(ethylene oxide) or copolymers of ethylene and propylene oxide. Pluronic gels are examples of such polymers, and exhibit thermosetting property that allows them to exist as viscous liquids at room temperature, but as gels at body temperature, as discussed previously. Other compositions for the injectable delivery compositions include the solutions of poly(propylene fumarate) (PPF) copolymers and pastes of calcium phosphate ceramics (see Schmitz et al., *J. Oral Maxillofacial Surgery* 57:1122 (1999), the entire teachings of which are incorporated herein by reference).

Implantable pharmaceutical compositions are beneficial especially for indications such as stimulating bone growth, cartilage growth or repair and cardiac repair. "Implantation" or "administration at a site" means in sufficient proximity to the site in need of treatment so that the desired healing occurs (e.g., an improved clinical outcome of the condition being treated in the presence of the drug compared with its absence) at the site when the thrombin peptide derivative is released from the pharmaceutical composition. It is understood that an implantable pharmaceutical composition may also be a sustained release formulation or an injectable formulation described previously. For example, implantable pharmaceutical compositions may also comprise a sustained release carrier to achieve slow and continuous medications at the implantation site.

The implantable pharmaceutical compositions can be shaped as desired in anticipation of surgery or shaped by the physician or technician during surgery. It is preferred to shape the matrix to span a tissue defect and to take the desired form of the new tissue. In the case of bone repair of a non-union defect, for example, it is desirable to use dimensions that span the non-union. In bone formation procedures, the material is slowly absorbed by the body and is replaced by bone in the shape of or very nearly the shape of the implant.

Alternatively, the implantable pharmaceutical composition can be partially enclosed in a supporting physical structure such as a mesh, wire matrix, stainless steel cage, threaded interbody fusion cage and the like before administering to the site, for example, in need of bone growth.

In yet another alternative, the disclosed pharmaceutical compositions especially for stimulating bone growth and cartilage repair or growth advantageously comprise carriers that include porous matrices which can then serve as a scaffolding for bone and tissue growth onto which bone progenitor cells and osteogenic cells may migrate and attach. Such carriers are said to be osteoconductive. For certain applications, the carrier should have sufficient mechanical strength to maintain its three dimensional structure and help support the immobilization of the bone or tissue segments being united or grafted together. Examples of suitable osteoconductive carriers include collagen (e.g., bovine collagen), fibrin, calcium phosphate ceramics (e.g., hydroxyapatite and tricalcium phosphate), calcium sulfate, guanidine-extracted allogenic bone and combinations thereof. A number of suitable carriers are commercially available, such as COLLAGRAFT® (Cohension Technologies, Inc., Palo Alto, Calif.), which is a mixture of hydroxyapatite, tricalcium phosphate and fibrillar collagen, and PRO OSTEON 500™ (Interpore Cross International, Irvine, Calif.), which is a hydroxyapatite biomatrix formed by the conversion of marine coral calcium carbonate to crystalline hydroxyapatite. Descriptions of synthetic biodegradable polymers that can serve as osteoconductive carriers with sustained release characteristics, can be found in Behravesh et al., *Clinical Orthopaedics* 367:S118 (1999) and Lichun et al., *Polymeric Delivery Vehicles for Bone Growth Factors* in "Controlled Drug Delivery—Designing Technologies for the Future" Park and Mrsny eds., American Chemical Society, Washington, D.C. (2000). The entire teachings of these references are incorporated herein by reference. Examples of the biodegradable polymers include poly ∀-hydroxy esters such as polylactic acid/polyglycolic acid homopolymers and copolymers, polyphosphazenes (PPHOS), polyanhydrides and poly(propylene fumarates), which are described above in detail.

Alternatively, the pharmaceutical compositions can be implanted to the site in the form of microparticles or microspheres. For example, the microparticles are placed in contact or in close proximity to the site in need of cardiac repair, bone growth, or cartilage repair either by surgically exposing the site and applying the microparticles on or in close proximity to the site by painting, pipetting, spraying, injecting or the like. Microparticles can also be delivered to the site by endoscopy or by laparoscopy. Poly(propylene fumarates) (PPF)

are highly desirable biocompatible implantable carriers for use in repairing bone defects because they are an injectable, in situ polymerizable, biodegradable material. PPF, combined with a vinyl monomer (N-vinyl pyrrolidinone) and an initiator (benzoyl peroxide), forms an injectable solution that can be polymerized in situ. It is particularly suited for filling skeletal defects of a wide variety of sizes and shapes (see Suggs et al., *Macromolecules* 30:4318 (1997), Peter et al., *J. Biomater. Sci. Poly,. Ed.* 10.363 (1999) and Yaszemski et al., *Tissue Eng.* 1:41 (1995), the entire teachings of which are incorporated herein by reference). The addition of solid phase components such as ョ-tricalcium phosphate and sodium chloride can improve the mechanical properties of PPF polymers (see Peter et al., *J. Biomed. Mater. Res.* 44:314 (1999), the entire teachings of which are incorporated herein by reference). Methods for encapsulating compositions (such as in a coating of hard gelatin or cyclodextran) are known in the art (Baker, et al., "Controlled Release of Biological Active Agents", John Wiley and Sons, 1986).

Diseases and conditions, treatable with the disclosed pharmaceutical composition comprising a thrombin peptide derivative, for example, wounds and angioplasty, are often accompanied by symptoms and infirmities such as pain and infection. In certain instances it may be advantageous to co-administer one or more additional pharmacologically active agents along with the pharmaceutical composition of the instant invention to address such issues. For example, managing pain and inflammation may require co-administration with analgesic or an anti-inflammatory agent. Managing infection may require co-administration with antimicrobial, antibiotic or disinfectant agents.

Thrombin peptide derivatives can be synthesized by solid phase peptide synthesis (e.g., BOC or FMOC) method, by solution phase synthesis, or by other suitable techniques including combinations of the foregoing methods. The BOC and FMOC methods, which are established and widely used, are described in Merrifield, *J. Am. Chem. Soc.* 88.2149 (1963); Meienhofer, *Hormonal Proteins and Peptides*, C. H. Li, Ed., Academic Press, 1983, pp. 48-267; and Barany and Merrifield, in *The Peptides*, E. Gross and J. Meienhofer, Eds., Academic Press, New York, 1980, pp. 3-285. Methods of solid phase peptide synthesis are described in Merrifield, R. B., *Science*, 232: 341 (1986); Carpino, L. A. and Han, G. Y., *J. Org. Chem.*, 37: 3404 (1972); and Gauspohl, H. et al., *Synthesis*, 5: 315 (1992)). The teachings of these six articles are incorporated herein by reference in their entirety.

The invention is illustrated by the following examples which are not intended to be limiting in any way.

EXEMPLIFICATION

Example 1

A Control Experiment Stability of TP508 in the Absence of a Dimerization Inhibitor TP508 was dissolved in 150 mM sterile saline to give a final concentration of 5 mg/ml. Samples (100 μl) were transferred to a 2 ml sterile Cryo tube and stored protected from light at 4° C. Samples were diluted to 1 mg/ml and analyzed by reverse phase HPLC using C18 column (Alltech Adsorbosphere XL column C18 90Å 5 μm 250 ×4.6 mm) at defined time points. A gradient method was performed in which mobile phase B is increased from 20% to 50% from 1-15 min (mobile phase A—0.1% TFA in water; mobile phase B—0.1% TFA in acetonitrile) and injection volume is 10 μl. TP508, TP508 dimer and unidentified peaks were identified and quantified from the area of the chromatogram.

TABLE 1

Stability of TP508 in the Absence of a Dimerization Inhibitor at 4° C. Mean Peak area, %

| Time (days) | TP508 | TP508 Dimer | Unidentified Peaks |
|---|---|---|---|
| 0 | 92.45 | 3.03 | 4.52 |
| 0.33 | 90.21 | 5.29 | 4.50 |
| 1 | 88.06 | 7.28 | 4.66 |
| 2 | 84.87 | 10.88 | 4.25 |
| 4 | 70.98 | 24.85 | 4.17 |
| 14 | 4.67 | 91.4 | 3.93 |
| 21 | 3.61 | 93.23 | 3.16 |
| 28 | 2.54 | 93.73 | 3.73 |
| 90 | 0 | 96.51 | 3.49 |
| 183 | 0 | 97.02 | 2.98 |
| 273 | 0 | 96.53 | 3.74 |
| 425 | 0 | 92.31 | 7.69 |

Example 2

Stability of TP508 in the Presence of a Chelating Agent

TP508 was dissolved at 1 mg/ml in buffered or unbuffered solutions, with or without EDTA. Solutions were incubated at room temperature and samples taken at intervals for analysis by HPLC. The percentage formation of dimer was calculated from the resulting chromatograms. The following solutions were used for dissolving TP508 (1 mg/mL):
PBS, pH 7.4 (sparged with N2 for 30 min)
10 mM Hepes, 150 mM NaCl, pH 7.0
10 mM Hepes, 150 mM NaCl, 5 mM EDTA, pH 7.0

One mL of each solution was placed into a 1.5 mL polypropylene microcentrifuge tube, and allowed to stand at room temperature. At defined intervals, 100 uL was removed for analysis by HPLC method mentioned in example 1. Percentage of dimers formed over time is summarized in Table 2.

TABLE 2

| | Percentage of Dimer | | | |
|---|---|---|---|---|
| | 0 min | 30 min | 60 min | 90 min |
| PBS | 4.8 | 8.8 | 14.3 | 26.7 |
| Hepes/NaCl | 5.7 | 13.3 | 31.3 | 53.9 |
| Hepes/NaCl/EDTA | 6.1 | 5.9 | 6.1 | 6.2 |

In phosphate buffered saline (PBS) or Hepes/NaCl the rate of dimer formation was very rapid. As shown, the addition of 5 mM EDTA greatly reduced the rate of dimer formation. These results suggest that dimer formation may be promoted by the presence of trace amounts of divalent ions since the formation of dimers is prevented or reduced by EDTA.

Example 3

Stability of TP508 in the Presence of a Dimerization Inhibitor, Thioglycerol, EDTA or the Combination of Both Samples prepared as described in Table 3 typically contained 50 ug/mL of TP508 dissolved in Pluronic gels. The samples were then stored over time at 4° C. For the analysis, the samples were diluted ten times with 0.1% TFA and analyzed by HPLC. Typically, 50 uL of the diluted sample was analyzed. Quantitation of TP508 was made by an external standard. A dual TP508 standard was analyzed prior to the sample analysis. One sample from each group of Table 3 was analyzed.

adduct. These results demonstrate that EDTA and thio-containing chemical can be used to stabilize TP508 from dimerization.

TABLE 3

Composition of Samples

| Ingredients | Supplier | Thioglycerol T | EDTA E | Thioglycerol/ EDTA TE | EDTA Blanket with N₂ EN |
|---|---|---|---|---|---|
| Citrate Buffer pH 5.5 | Prepared in the lab using citric acid + NaOH | 82% | 82.496% | 82.3996% | 82.496% |
| Benzyl Alcohol, NF | Spectrum | 0.5% | 0.5% | 0.5% | 0.5% |
| Pluronic F-127 | Spectrum | 17% | 17% | 17% | 17% |
| Monothioglycerol | Spectrum | 0.5% | N/A | 0.1% | N/A |
| EDTA Disodium | Spectrum | N/A | 0.004% | 0.0004% | 0.004% |
| Final pH | N/A | 5.7 | 5.7 | 5.7 | 5.7 |

T—Thioglycerol
E—EDTA
TE—Thioglycerol/EDTA
EN—EDTA with N₂

Figure 1:
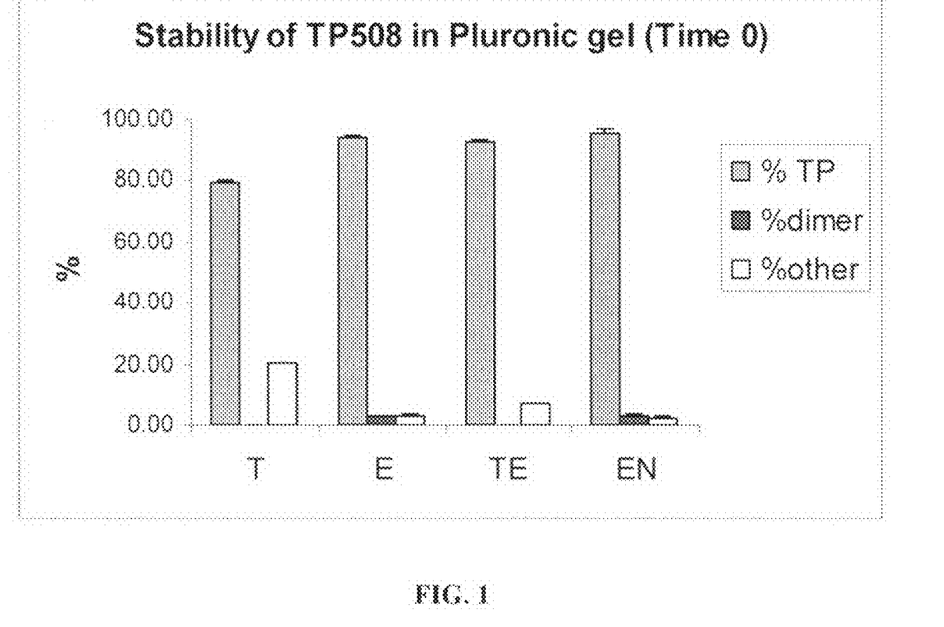
FIG. 1 is a graph showing TP508 monomer, dimer, and other (aducts, etc.) at time of mixing (Time 0) with dimerization inhibitor (Thioglycerol (T), EDTA (E), Thioglycerol and EDTA (TE), and EDTA under N$_2$ (EN).

Time 0:

As shown in FIG. 1, very low concentration of dimer was observed at time 0 for the all samples prepared as described in Table 3. Unknown peaks comprising about 20% and 6% of the total sample were observed in the samples containing thioglycerol (Group T) and thioglycerol/EDTA (Group TE), respectively. These unknown peaks had a retention time slightly larger than that of TP508, suggesting that they could correspond to an adduct of TP508 and thioglycerol since the amount of adduct formation is somewhat proportional to the thioglycerol content in the two samples.

Figure 2:
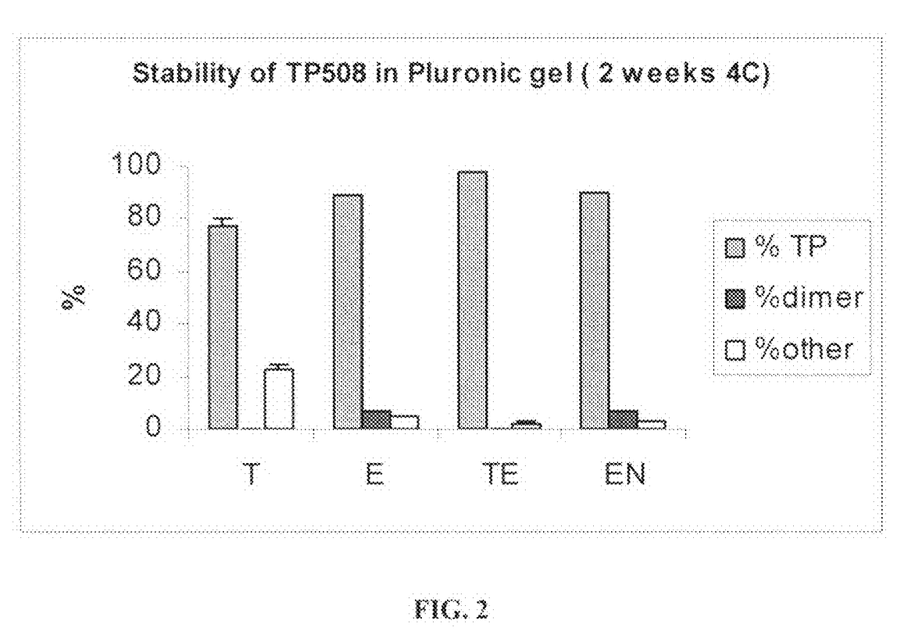
FIG. 2 is a graph showing stability of TP508 in Pluronic gels after 2 weeks storage at 4 degrees C. in the presence of dimerization inhibitor (Thioglycerol (T), EDTA (E), Thioglycerol and EDTA (TE), and EDTA under N$_2$ (EN).

Two-week's Storage at 4° C.:

Samples stored for two weeks at 4° C. showed essentially the same concentration of dimers as that at time 0, as shown in FIG. 2. In the sample containing EDTA (Group E) or EDTA w/ N₂ (Group EN), over 90% of TP508 still retained its monomeric form.

Figure 3:
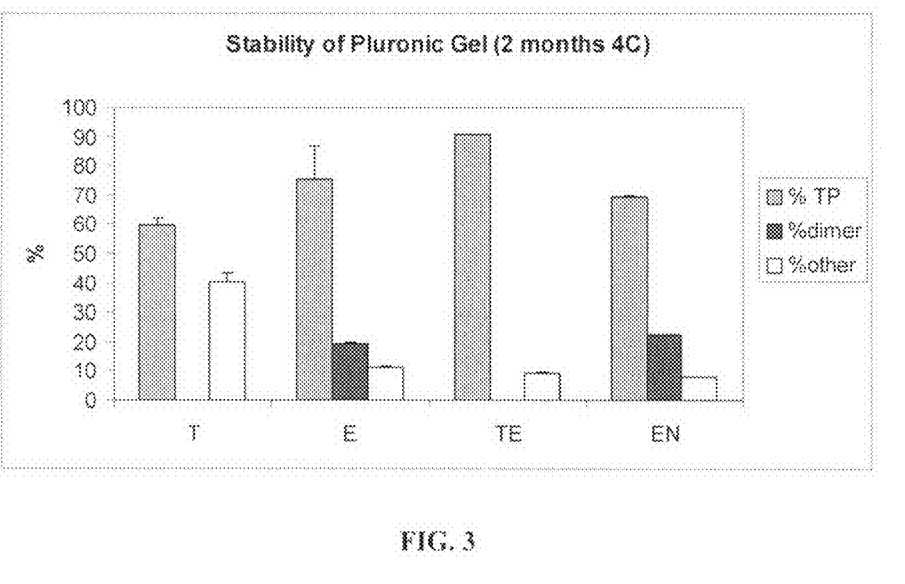
FIG. 3 is a graph showing stability of TP508 in Pluronic gels after two-months storage at 4° C. in the presence of dimerization inhibitor (Thioglycerol (T), EDTA (E), Thioglycerol and EDTA (TE), and EDTA under N$_2$ (EN).

Two-month's Storage at 4° C.:

As shown in FIG. 3, all the samples containing a dimerization inhibitor (Group T, E, TE and EN) showed increased stability of TP508 as compared to the samples without a dimerization inhibitor. The sample containing both thioglycerol and EDTA (Group TE) showed essentially the same amount of dimers as that at time 0, indicating that TP508 retained its monomeric form essentially free of dimers even after two-month's storage in the presence of both thioglycerol and EDTA with only 10% of TP508-thioglycerol adduct. Approximately 80% of TP508 remained as a monomer in the sample containing EDTA (Group E) or EDTA w/ N₂ (Group EN). Having a nitrogen blanket during the preparation of gels does not appear to affect dimerization. The sample containing thioglycerol (Group T) showed that approximately 60% of TP508 retained its monomeric form and the remaining approximately 40% of TP508 formed a TP508-thioglycerol Example 4

Stability of TP508 in the Presence of a EDTA and an Antioxidant

The following antioxidants were tested for their ability to inhibit TP508 dimerization in combination with EDTA. The normal % used in formulation is shown in the following Table 4:

TABLE 4

Compositions of Samples

| Antioxidants | Low | High |
|---|---|---|
| Ascorbic acid | 0.1 | 1.0 |
| Thioglycollic acid | 0.05 | 0.2 |
| Cysteine hydrochloride | 0.1 | 0.5 |
| Methionine | 0.1 | 0.5 |

A gel base (17% Pluronic, 0.0004% EDTA and citrate buffer, pH 5.0 with preservatives) was prepared and used. Each type of antioxidant (either low or high %) was added at the desired concentration. Then, TP508 was added to the gel to give a concentration of 50 μg/ml. Samples were incubated at 4° C. for 3 weeks. Then, 100 μl of sample was diluted with 900 μl 0.1% TFA and analyzed by HPLC according to the method described in Example 1. A dual standard was analyzed prior to sample analysis. Also, a blank gel with preservatives and antioxidant was analyzed.

The results are shown below in Table 5. In short, TP508 was very stable at a high concentration of antioxidants at 4° C. for three weeks. With the exception of ascorbic acid, low concentrations of antioxidants were also effective.

TABLE 5

Concentration of TP508 (μg/ml) Over Time

| Ascorbic acid | 1% | 0.1% |
|---|---|---|
| Time 0 | 43.4 μg/ml | 39.6 μg/ml |
| 3 weeks (4° C.) | 44.0 μg/ml | 23.8 μg/ml |

TABLE 5-continued

Concentration of TP508 (μg/ml) Over Time

| Thioglycollic acid | 0.2% | 0.05% |
|---|---|---|
| Time 0 | 46.7 μg/ml | 47.1 μg/ml |
| 3 weeks (4° C.) | 46.8 μg/ml | 43.7 μg/ml |
| Cysteine hydrochloride | 0.5% | 0.1% |
| Time 0 | 51.5 μg/ml | 49.8 μg/ml |
| 3 weeks (4° C.) | 48.9 μg/ml | 53.3 μg/ml |
| Methionine | 0.5% | 0.1% |
| Time 0 | 46.9 μg/ml | 45.3 μg/ml |
| 3 weeks (4° C.) | 51.6 μg/ml | 48.8 μg/ml |

Example 5

Stability of TP508 in the Presence of a Chelating Agent (EDTA) and an Antioxidant Over Various pH Ranges Preparations of buffered samples with 10 μM EDTA at different pH and at pH 5.5 with addition of antioxidants were tested for their ability to inhibit TP508 dimerization and formation of other molecular forms. The samples tested at various pH and percent oxidant are shown in Table 6.

TABLE 6

Compositions of Test Samples

| Groups: | Conditions: |
|---|---|
| 1 | pH 4.5 |
| 2 | pH 5.0 |
| 3 | pH 5.5 |
| 4 | pH 5.5, 0.5% (w/v) cysteine |
| 5 | pH 5.5, 0.5% (w/v) methionine |
| 6 | pH 5.5, 0.2% (v/v) thioglycolic acid |
| 7 | pH 6.0 |

TP508 was prepared in citrate buffer 50 mM from pH 4.5 to 6.0 with 10 μM EDTA. Samples were filter-sterilized and incubated at room temperature away from any light source. At indicated time points, each sample was analyzed by HPLC to determine TP508 monomer concentration (Table 7), dimer percentage (Table 8), percentage of adduct (Table 9), and unknown molecular entities (Table 10).

TABLE 7

Concentration of TP508 (μg/mL) from time 0 to day 28

| Conditions: | Time 0 | Day 4 | Day 12 | Day 28 |
|---|---|---|---|---|
| pH 4.5 | 48.03 | 45.13 | 43.27 | 37.77 |
| pH 5.0 | 50.50 | 48.35 | 47.99 | 44.26 |
| pH 5.5 | 52.07 | 48.51 | 48.76 | 45.61 |
| pH 5.5, 0.5% (w/v) cysteine | 50.35 | 41.55 | 32.85 | 31.77 |
| pH 5.5, 0.5% (w/v) methionine | 51.29 | 48.96 | 49.18 | 45.79 |
| pH 5.5, 0.2% (v/v) thioglycolic acid | 48.57 | 41.28 | 38.54 | 30.29 |
| pH 6.0 | 50.95 | 48.64 | 50.86 | 46.21 |

TABLE 8

Dimer % from time 0 to day 28

| Conditions: | Time 0 | Day 4 | Day 12 | Day 28 |
|---|---|---|---|---|
| pH 4.5 | 0.66 | 1.92 | 3.44 | 6.75 |
| pH 5.0 | 0.77 | 1.22 | 1.42 | 1.93 |
| pH 5.5 | 0.73 | 1.40 | 1.76 | 2.69 |
| pH 5.5, 0.5% (w/v) cysteine | 0.00 | 0.00 | 0.00 | 0.00 |
| pH 5.5, 0.5% (w/v) methionine | 0.80 | 1.10 | 1.36 | 1.38 |
| pH 5.5, 0.2% (v/v) thioglycolic acid | 0.00 | 0.00 | 0.00 | 0.00 |
| pH 6.0 | 0.87 | 1.66 | 2.13 | 3.38 |

TABLE 9

Others % + adduct peak % from time 0 to day 28

| Conditions: | Time 0 | Day 4 | Day 12 | Day 28 |
|---|---|---|---|---|
| pH 4.5 | 0.00 | 1.83 | 3.72 | 13.69 |
| pH 5.0 | 0.00 | 1.33 | 2.72 | 10.06 |
| pH 5.5 | 0.00 | 0.79 | 1.28 | 6.55 |
| pH 5.5, 0.5% (w/v) cysteine | 1.63 | 16.32 | 31.86 | 34.73 |
| pH 5.5, 0.5% (w/v) methionine | 0.00 | 0.80 | 1.31 | 7.22 |
| pH 5.5, 0.2% (v/v) thioglycolic acid | 4.85 | 15.62 | 21.36 | 38.97 |
| pH 6.0 | 0.00 | 0.87 | 0.45 | 5.18 |

TABLE 10

Rate of dimer and unknown formation

| pH | Rate of Dimerization | Rate of Unknown Formation |
|---|---|---|
| 4.5 | 0.2121 | 0.4862 |
| 5.0 | 0.0376 | 0.3574 |
| 5.5 | 0.0644 | 0.2328 |
| 6.0 | 0.0835 | 0.1791 * |
| 5.5 + Met | 0.0183 * | 0.2574 |

* Lowest values

Results demonstrate that all antioxidants tested in this study prevent or reduce dimerization of TP508 as shown in Table 8 relative to that formed in citrate buffers ranging in pH from 4.5 to 6.0. Results in Table 9 show that methionine is unable to create TP508 adducts due to lack of a thiol group. These results suggest that the best pH to inhibit dimer formation of TP508 was at pH 6.0 from this experiment without any antioxidant. With the addition of 0.5% (w/v) methionine at pH 5.5, the slowest rate was obtained (0.0183) shown in table 10. The rate of unknown formation is inversely proportional to the pH from 4.5 to 6.0, indicating TP508 is prone to acid hydrolysis at this buffer system. Also, methionine in this experiment did not prevent or cause the unknown formation. In short, methionine appears to be the best antioxidant to prevent or reduce dimerization of TP508 without forming TP508 adducts and the slowest rate of unknown peak formation was at pH 6.0 in this experiment.

Example 6

Effect of Divalent Chelators on TP508 Dimerization

The divalent chelating agents, diethylenetriaminepentacetic acid (DTPA) and bathophenanthroline disulfonic acid (BPADA), which are known to chelate a copper ion, were tested for their ability to inhibit TP508 dimer formation.

Conditions:
A. 50 mM acetate/100 mM NaCl, pH 5.4
B. 50 mM acetate/100 mM NaCl, pH 5.4 with 10 uM DTPA
C. 50 mM acetate/100 mM NaCl, pH 5.4 with 10 uM BPADA Procedures:
TP508 (10 ug/mL) was incubated with or without the chelators in polypropylene centrifuge tubes at room temperatures and analyzed at the indicated time points by capillary electrophoresis to monitor any dimer formation.

Results:

TABLE 11

Percent dimer from Sample A: 50 mM acetate/100 mM NaCl, pH 5.4

| Time | % Dimer |
| --- | --- |
| 2 min | 0 |
| 1 hr | 17 |
| 3.5 hr | 30 |
| 4.5 hr | 37 |
| 5.5 hr | 47 |
| 21 hr | 81 |
| 28 hr | 74 |
| 4 days | 100 |
| 5 days | 100 |

TABLE 12

Precent dimer from Sample B: 50 mM acetate/100 mM NaCl, pH 5.4 with 10 uM DTPA

| Time | % Dimer |
| --- | --- |
| 22 min | 0 |
| 2.5 hr | 0 |
| 4 hr | 0 |
| 5 hr | 0 |
| 6 hr | 0 |
| 21 hr | 0 |
| 28 hr | 0 |
| 4 days | 0 |
| 5 days | 0 |

TABLE 13

Percent dimer from Sample C: 50 mM acetate/100 mM NaCl, pH 5.4 with 10 uM BPADA

| Time | % Dimer |
| --- | --- |
| 40 min | 0 |
| 3 hr | 0 |
| 4 hr | 0 |
| 5 hr | 41 |
| 6 hr | 0 |
| 22 hr | 0 |
| 29 hr | 0 |
| 4 days | 0 |
| 5 days | 17 |

These results demonstrate that chelators other than EDTA can also stabilize TP508 to prevent or reduce dimer formation.

Example 7

Preparation of TP508 in Pluronic Gels

TP508 (3.60 mg, Bachem Fmoc) was added to Pluronic gels (72 mL), resulting in a concentration of 50 ug/mL in a 100 mL glass beaker with a magnetic stir bar. The gels were stirred at 4° C. for 1 hour to facilitate complete mixing. For Sample D, gels were stirred under a nitrogen atmosphere using a nitrogen gas blanket. Gels were then filled to the rim of a 1 mL polypropylene vial. The vial was capped with a Teflon lined cap to prevent introduction of any air bubble in the gels. Samples were stored at either 4° C. or in the drawer (25° C.) away from light.

In a commercial formulation, TP508 could be added to a fully formulated gel or to an intermediate phase containing appropriate stabilizers as described in Example 3, Table 3.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method for activating the non-proteolytically activated thrombin receptor in a subject in need of such treatment, said method comprising administering to the subject an effective amount of a pharmaceutical composition comprising:
   a) a 23 amino acid polypeptide, wherein the amino acid of the polypeptide is Ala-Gly-Tyr-Lys-Pro-Asp-Glu-Gly-Lys-Arg-Gly-Asp-Ala-Cys-Glu-Gly-Asp-Ser-Gly-Gly-Pro-Phe-Val (SEQ ID NO:3); and
   b) a chelating agent for binding to a metal ion; and/or a pharmaceutically acceptable thiol-containing compound.

2. The method of claim 1 wherein the pharmaceutical composition additionally comprises an antioxidant.

3. The method of claim 2, wherein the antioxidant is selected from the group consisting of tocopherol, methionine, glutathione, tocotrienol, dimethyl glycine, betaine, butylated hydroxyanisole, butylated hydroxytoluene, turmerin, vitamin E, ascorbic acid, ascorbyl palmitate and thioglycolic acid.

4. The method of claim 2, wherein the pharmaceutical composition comprises a chelating agent for binding to a metal ion; and an antioxidant.

5. The method of claim 4, wherein the antioxidant is methionine.

6. The method of claim 1, wherein the pharmaceutical composition comprises a copper-chelating agent.

7. The method of claim 6, wherein the copper-chelating agent is selected from the group consisting of diethylenetriaminepentacetic acid (DTPA) and bathophenanthroline disulfonic acid (BPADA).

8. The method of claim 6, wherein the copper-chelating agent is selected from the group consisting of ethylenediaminetetraacetic acid (EDTA), penicillamine, trientine, N,N'-diethyldithiocarbamate (DDC), 2,3,2'-tetraamine (2,3,2'-tet), neocuproine, N,N,N',N'-tetrakis(2-pyridylmethyl)ethylenediamine (TPEN), 1,10-phenanthroline (PHE), tetraethylenepentamine, triethylenetetraamine and tris(2-carboxyethyl) phosphine (TCEP).

9. The method of claim 6 wherein the pharmaceutical composition comprises a pharmaceutically acceptable thiol-containing compound.

10. The method of claim 1, wherein the pharmaceutical composition comprises a pharmaceutically acceptable thiol-containing compound selected from the group consisting of thioglycerol, mercaptoethanol, thioglycol, thiodiglycol, thioglucose, dithiothreitol (DTT), and dithio-bis-maleimidoethane (DTME).

11. The method of claim 1, wherein the subject is in need of treatment to promote cartilage growth or repair.

12. The method of claim 1, wherein the subject is in need of bone growth.

13. The method of claim 1, wherein the subject is in need of treatment to promote wound healing.

14. The method of claim 13, wherein the wound is a chronic wound.

15. The method of claim 1 wherein the subject is in need of treatment to promote cardiac repair or inhibit restenosis.

16. A method for activating the non-proteolytically activated thrombin receptor in a subject in need of such treatment, said method comprising the step of administering to the subject an effective amount of a pharmaceutical composition, the pharmaceutical composition comprising:
   a) a thrombin peptide derivative, wherein the throbin peptide dervative is the polypeptide: Ala-Gly-Tyr-Lys-Pro-Asp-Glu-Gly-Lys-Arg-Gly-Asp-Ala-Cys-Glu-Gly-Asp-Ser-Gly-Gly-Pro-Phe-Val-$NH_2$ (SEQ ID NO:4); and
   b) a chelating agent for binding to a metal ion; and/or a pharmaceutically acceptable thiol-containing compound.

17. The method of claim 16, wherein the pharmaceutical composition further comprises an antioxidant.

18. The method of claim 16, wherein the pharmaceutical composition comprises a copper chelating agent.

19. The method of claim 16, wherein the subject is in need of treatment to promote cartilage growth or repair.

20. The method of claim 16, wherein the subject is in need of bone growth.

21. The method of claim 16, wherein the subject is in need of treatment to promote wound healing.

22. The method of claim 21, wherein the wound is a chronic wound.

23. The method of claim 16, wherein the subject is in need of treatment to promote cardiac repair or inhibit restenosis.

* * * * *

SEQUENCE LISTING

```
<160> NUMBER OF SEQ ID NOS: 8

<210> SEQ ID NO 1
<211> LENGTH: 23
<212> TYPE: PRT
<213> ORGANISM: Artificial Sequence
<220> FEATURE:
<223> OTHER INFORMATION: Synthetic Peptide
<220> FEATURE:
<221> NAME/KEY: VARIANT
<222> LOCATION: 1
```

```
<223> OTHER INFORMATION: Alanine at position 1 is optionally N-acylated
<220> FEATURE:
<221> NAME/KEY: VARIANT
<222> LOCATION: 23
<223> OTHER INFORMATION: Valine at position 23 is optionally C-amidated

<400> SEQUENCE: 1

Ala Gly Tyr Lys Pro Asp Glu Gly Lys Arg Gly Asp Ala Cys Glu Gly
 1               5                  10                  15

Asp Ser Gly Gly Pro Phe Val
            20

<210> SEQ ID NO 2
<211> LENGTH: 23
<212> TYPE: PRT
<213> ORGANISM: Artificial Sequence
<220> FEATURE:
<223> OTHER INFORMATION: Synthetic Peptide
<220> FEATURE:
<221> NAME/KEY: VARIANT
<222> LOCATION: 1
<223> OTHER INFORMATION: Alanine at position 1 is optionally N-acylated
<220> FEATURE:
<221> NAME/KEY: VARIANT
<222> LOCATION: 15
<223> OTHER INFORMATION: Xaa = Glu or Gln
<220> FEATURE:
<221> NAME/KEY: VARIANT
<222> LOCATION: 22
<223> OTHER INFORMATION: Xaa = Phe, Met, Leu, His or Val
<220> FEATURE:
<221> NAME/KEY: VARIANT
<222> LOCATION: 23
<223> OTHER INFORMATION: Valine at position 23 is optionally C-amidated

<400> SEQUENCE: 2

Ala Gly Tyr Lys Pro Asp Glu Gly Lys Arg Gly Asp Ala Cys Xaa Gly
 1               5                  10                  15

Asp Ser Gly Gly Pro Xaa Val
            20

<210> SEQ ID NO 3
<211> LENGTH: 23
<212> TYPE: PRT
<213> ORGANISM: Artificial Sequence
<220> FEATURE:
<223> OTHER INFORMATION: Fragment of Human Thrombin

<400> SEQUENCE: 3

Ala Gly Tyr Lys Pro Asp Glu Gly Lys Arg Gly Asp Ala Cys Glu Gly
 1               5                  10                  15

Asp Ser Gly Gly Pro Phe Val
            20

<210> SEQ ID NO 4
<211> LENGTH: 23
<212> TYPE: PRT
<213> ORGANISM: Artificial Sequence
<220> FEATURE:
<223> OTHER INFORMATION: Synthetic Peptide
<220> FEATURE:
<221> NAME/KEY: VARIANT
<222> LOCATION: 1
<223> OTHER INFORMATION: Alanine is unsubstituted
<220> FEATURE:
<221> NAME/KEY: VARIANT
<222> LOCATION: 23
<223> OTHER INFORMATION: Valine at position 23 is amidated with NH2

<400> SEQUENCE: 4
```

```
Ala Gly Tyr Lys Pro Asp Glu Gly Lys Arg Gly Asp Ala Cys Glu Gly
 1               5                  10                  15

Asp Ser Gly Gly Pro Phe Val
            20
```

<210> SEQ ID NO 5
<211> LENGTH: 33
<212> TYPE: PRT
<213> ORGANISM: Artificial Sequence
<220> FEATURE:
<223> OTHER INFORMATION: Synthetic Peptide
<220> FEATURE:
<221> NAME/KEY: VARIANT
<222> LOCATION: 1
<223> OTHER INFORMATION: Aspartic acid at position 1 is optionally
      N-acylated
<220> FEATURE:
<221> NAME/KEY: VARIANT
<222> LOCATION: 33
<223> OTHER INFORMATION: Phenylalanine at position 33 is optionally
      C-amidated

<400> SEQUENCE: 5

```
Asp Asn Met Phe Cys Ala Gly Tyr Lys Pro Asp Glu Gly Lys Arg Gly
 1               5                  10                  15

Asp Ala Cys Glu Gly Asp Ser Gly Gly Pro Phe Val Met Lys Ser Pro
            20                  25                  30

Phe
```

<210> SEQ ID NO 6
<211> LENGTH: 33
<212> TYPE: PRT
<213> ORGANISM: Artificial Sequence
<220> FEATURE:
<223> OTHER INFORMATION: Synthetic Peptide
<220> FEATURE:
<221> NAME/KEY: VARIANT
<222> LOCATION: 1
<223> OTHER INFORMATION: Aspartic acid at position is optionally
      N-acylated
<220> FEATURE:
<221> NAME/KEY: VARIANT
<222> LOCATION: 20
<223> OTHER INFORMATION: Xaa = Glu or Gln
<220> FEATURE:
<221> NAME/KEY: VARIANT
<222> LOCATION: 27
<223> OTHER INFORMATION: Xaa = Phe, Met, Leu, His or Val
<220> FEATURE:
<221> NAME/KEY: VARIANT
<222> LOCATION: 33
<223> OTHER INFORMATION: Phenylalanine at position 33 is optionally
      C-amidated

<400> SEQUENCE: 6

```
Asp Asn Met Phe Cys Ala Gly Tyr Lys Pro Asp Glu Gly Lys Arg Gly
 1               5                  10                  15

Asp Ala Cys Xaa Gly Asp Ser Gly Gly Pro Xaa Val Met Lys Ser Pro
            20                  25                  30

Phe
```

<210> SEQ ID NO 7
<211> LENGTH: 23
<212> TYPE: PRT
<213> ORGANISM: Artificial Sequence
<220> FEATURE:
<223> OTHER INFORMATION: Synthetic Peptide
<220> FEATURE:

```
<221> NAME/KEY: VARIANT
<222> LOCATION: 1
<223> OTHER INFORMATION: Alanine at position 1 is unsubstituted
<220> FEATURE:
<221> NAME/KEY: VARIANT
<222> LOCATION: 23
<223> OTHER INFORMATION: Valine at position 23 is unsubstituted

<400> SEQUENCE: 7

Ala Gly Tyr Lys Pro Asp Glu Gly Lys Arg Gly Asp Ala Cys Glu Gly
 1               5                  10                  15

Asp Ser Gly Gly Pro Phe Val
             20

<210> SEQ ID NO 8
<211> LENGTH: 10
<212> TYPE: PRT
<213> ORGANISM: Artificial Sequence
<220> FEATURE:
<223> OTHER INFORMATION: Fragment of serine asterase conserved sequence

<400> SEQUENCE: 8

Cys Glu Gly Asp Ser Gly Gly Pro Phe Val
 1               5                  10
```